US00PP29416P3

(12) United States Plant Patent
Smit

(10) Patent No.: US PP29,416 P3
(45) Date of Patent: Jun. 19, 2018

(54) ***PEPEROMIA* PLANT NAMED 'NAPOLI NIGHTS'**

(50) Latin Name: ***Peperomia* hybrid**
Varietal Denomination: Napoli Nights

(71) Applicant: Obed Jacob Smit, Sappemeer (NL)

(72) Inventor: Obed Jacob Smit, Sappemeer (NL)

(73) Assignee: Eden CollecTion B.V., Sappemeer (NL)

( * ) Notice: Subject to any disclaimer, the term of this patent is extended or adjusted under 35 U.S.C. 154(b) by 0 days. days.

(21) Appl. No.: 15/330,400

(22) Filed: Sep. 15, 2016

(65) Prior Publication Data

US 2018/0077841 P1 Mar. 15, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

UPOV-PLUTO: Plant Variety Database ; citation for 'Napoli Nights' Retrieved on Oct. 31, 2017 (1 page total).*

* cited by examiner

*Primary Examiner* — Susan McCormick Ewoldt

(57) ABSTRACT

A new cultivar of *Peperomia* plant named 'Napoli Nights' that is characterized by leaves that have a grey-green colored pattern on the upper surface and are pink-red on the lower surface.

1 Drawing Sheet

Botanical classification: *Peperomia* hybrid.
Variety denomination: 'Napoli Nights'.

BACKGROUND OF THE INVENTION

The present invention relates to a new and distinct cultivar of *Peperomia* plant botanically known as *Peperomia* hybrid and hereinafter referred to by the cultivar name 'Napoli Nights'.

'Napoli Nights' originated from the crossing of the female or seed parent, an unnamed *Peperomia peruviana* cultivar and the male or pollen parent, an unnamed *Peperomia marmorata* cultivar. The crossing was conducted in 2013 in Sappemeer, Netherlands. The resulting seeds were subsequently planted and grown. The cultivar 'Napoli Nights' was selected by the inventor in 2014 in a controlled environment as a single plant within the progeny of the stated cross in a cultivated area of Sappemeer, Netherlands.

Asexual reproduction of the new cultivar 'Napoli Nights' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Napoli Nights'. These traits in combination distinguish 'Napoli Nights' as a new and distinct cultivar apart from other existing varieties of *Peperomia* known by the inventor.

1. *Peperomia* 'Napoli Nights' exhibits leaves that have a grey-green colored pattern on the upper surface and are pink-red on the lower surface.

The closest comparison cultivars are *Peperomia* 'Eden Rosso' (U.S. Plant Pat. No. 24,379) and *Peperomia* 'Sunrise' (U.S. application Ser. No. 15/330,448) 'Napoli Nights' is distinguishable from 'Eden Rosso' by the following characteristics:

1. *Peperomia* 'Napoli Nights' exhibits leaves having an upper surface with a grey-green colored pattern. In comparison, the upper leaf surface of 'Eden Rosso' is green.
2. *Peperomia* 'Napoli Nights' exhibits leaves having a lower surface that is pink-red. In comparison, the leaf lower surface of 'Eden Rosso' is red.

'Napoli Nights' is distinguishable from 'Sunrise' by the following characteristics:

1. *Peperomia* 'Napoli Nights' exhibits larger leaves than the leaves of 'Sunrise'.

'Napoli Nights' is distinguishable from the female parent plant by the following characteristics:

1. The leaves of 'Napoli Nights' are more oval in shape than the leaves of the female parent plant. In comparison, the leaves of the female parent plant are more rounded.
2. The upper surface of the leaves of 'Napoli Nights' exhibit a grey-green pattern. In comparison, the upper surface of the leaves of the female parent plant are green.

'Napoli Nights' is distinguishable from the male parent plant by the following characteristics:

1. The leaves of 'Napoli Nights' are less elongated than the leaves of the male parent plant.

2. The upper surface of the leaves of 'Napoli Nights' exhibit a grey-green pattern. In comparison, the upper surface of the leaves of the male parent plant are dark green.
3. The lower surface of the leaves of 'Napoli Nights' are pink-red. In comparison, the lower surface of the leaves of the male parent plant are red.

BRIEF DESCRIPTION OF THE DRAWING

The accompanying photograph illustrates the distinguishing traits of *Peperomia* 'Napoli Nights'. The photograph shows an overall view of a 35 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Napoli Nights'. Data was collected in Sappemeer, Netherlands from 35 week old plants grown in a glass greenhouse in 15 cm. diameter containers. The time of year was Winter and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Napoli Nights' has not been tested under all possible conditions and phenotypic differences may be observed with variations in environmental, climatic, and cultural conditions, however, without any variance in genotype.

Botanical classification: *Peperomia* hybrid 'Napoli Nights'.
Annual or perennial: Perennial.
Parentage: 'Napoli Nights' is a hybrid of the female parent, an unidentified *Peperomia peruviana* cultivar and the male parent an unidentified *Peperomia marmorata* cultivar.
Plant type: Potted plant.
Growth habit: Rosette.
Plant shape: Flattened globe shaped.
Suitable container size: 7 cm. pots or larger.
Plant height: 9.5 cm.
Plant width: 18.3 cm.
Vigor: Moderate.
Low temperature tolerance: 5° Centigrade.
High temperature tolerance: 40° Centigrade.
Propagation: Leaf cuttings.
Time to initiate roots (summer): 10 days at 18 to 20° C.
Time to initiate roots (winter): 14 days at 18 to 20° C.
Time to produce a rooted cutting (summer): 80 days at 18 to 20° C.
Time to produce a rooted cutting (winter): 100 days at 18 to 20° C.
Growth rate: Moderate.
Crop time: Approximately 30 to 35 weeks in Sappemeer, Netherlands.
Root system: Fibrous.
Plant fragrance: None.
Stem:
- *Branching habit.*—Short thick stems branching into rosettes of leaves.
- *Number of main stems per plant.*—Average 10.
- *Number of lateral branches per plant.*—Average 40.
- *Lateral branch dimensions.*—1.6 cm. in length and 0.5 cm. in width.
- *Internode length.*—0.10 cm.
- *Stem shape.*—Rounded.
- *Stem texture.*—Smooth.
- *Stem pubescence.*—Absent.
- *Stem angle.*—Vertical, zero degrees.
- *Stem strength.*—Strong.
- *Stem color* (*young*).—148A.
- *Stem color* (*mature*).—148A.
- *Internode color.*—148A.

Foliage:
- *Leaf arrangement.*—Rosette.
- *Compound or single.*—Single.
- *Quantity of leaves per main stem.*—Average 50.
- *Leaf shape.*—Ovate.
- *Leaf aspect.*—Convex to carinate.
- *Leaf apex.*—Acute.
- *Leaf base.*—Cordate.
- *Leaf dimensions.*—4.1 cm. in length and 2.3 cm. in width.
- *Texture.*—Glabrous (both surfaces).
- *Leaf luster.*—Glossy (both surfaces).
- *Pubescence.*—Absent.
- *Leaf margin.*—Entire.
- *Venation pattern.*—Parallel, furrowed.
- *Young leaf color* (*upper surface*).—N189B, surrounding veins N189A.
- *Young leaf color* (*lower surface*).—182B, surrounding veins 176B.
- *Mature leaf color* (*upper surface*).—189A.
- *Mature leaf color* (*lower surface*).—176B.
- *Vein color* (*upper surface*).—139A.
- *Vein color* (*lower surface*).—200C.

Petiole:
- *Petiole dimensions.*—5.8 cm. in length and 0.3 cm. in diameter.
- *Petiole texture.*—Glabrous.
- *Petiole luster.*—Slightly glossy.
- *Petiole pubescence.*—Absent.
- *Petiole strength.*—Low.
- *Petiole color.*—145C with fine stripes 181B.

Flower: 'Napoli Nights' has not produced flowers to date.
Fruit and seed: 'Napoli Nights' has not produced fruit or seed to date.
Disease and pest resistance: Disease and pest resistance has not been observed.

The invention claimed is:

1. A new and distinct variety of *Peperomia* plant named 'Napoli Nights' as described and illustrated.

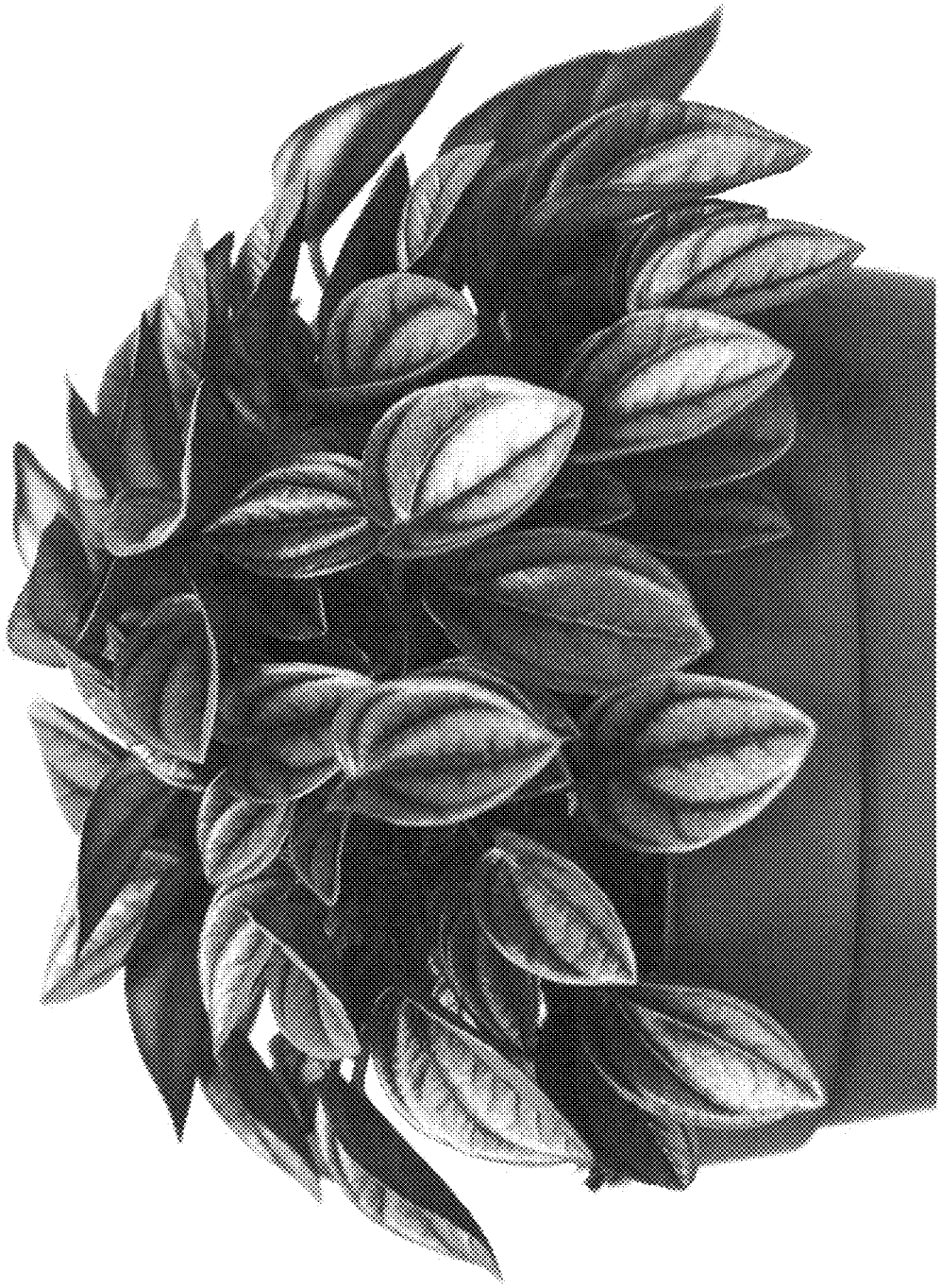

* * * * *